(12) United States Patent
Bertling et al.

(10) Patent No.: US 7,067,253 B1
(45) Date of Patent: *Jun. 27, 2006

(54) METHOD AND DEVICE FOR IDENTIFYING A POLYMER

(75) Inventors: Wolf Bertling, Erlangen (DE); Jorg Hassmann, Erlangen (DE)

(73) Assignee: november Aktiengesellschaft Gesellschaft für Molekulare Medizin, Erlangen (DE)

( * ) Notice: Subject to any disclaimer, the term of this patent is extended or adjusted under 35 U.S.C. 154(b) by 671 days.

This patent is subject to a terminal disclaimer.

(21) Appl. No.: 10/018,449

(22) PCT Filed: Jun. 10, 2000

(86) PCT No.: PCT/DE00/01945

§ 371 (c)(1),
(2), (4) Date: May 3, 2002

(87) PCT Pub. No.: WO00/77496

PCT Pub. Date: Dec. 21, 2000

(30) Foreign Application Priority Data

Jun. 14, 1999 (DE) ................................ 199 27 051

(51) Int. Cl.
*C12Q 1/68* (2006.01)
*G01N 33/53* (2006.01)
*C12M 1/00* (2006.01)

(52) U.S. Cl. .................. 435/6; 435/7.1; 435/283.1
(58) Field of Classification Search .............. 435/6, 435/7.1, 283.1; 536/24.3, 23.1
See application file for complete search history.

(56) References Cited

U.S. PATENT DOCUMENTS

| 4,687,732 A | 8/1987 | Ward et al. |
| 5,485,277 A | 1/1996 | Foster |
| 5,686,071 A | 11/1997 | Subramanian et al. |
| 6,669,906 B1 * | 12/2003 | Schalkhammer et al. ..... 422/50 |

FOREIGN PATENT DOCUMENTS

| DE | 196 21 312 A1 | 12/1997 |
| EP | 0 762 122 A1 | 3/1997 |
| FR | 2 762 394 | 10/1998 |
| WO | WO 91/02981 | 3/1991 |
| WO | WO 97/04129 | 2/1997 |
| WO | WO 98/48275 | * 10/1998 |

OTHER PUBLICATIONS

International Search Report (mailed Oct. 10, 2002).*
International Search Report Oct. 10, 2000.

* cited by examiner

Primary Examiner—Ethan Whisenant
(74) Attorney, Agent, or Firm—Fish & Richardson P.C.

(57) ABSTRACT

The invention relates to a method for identifying a first polymer (4, 7) which is bonded to a first phase (5) that reflects electromagnetic waves. Said method comprises the following steps: (a) bringing the first polymer (4, 7) into contact with a second polymer (3, 8), which is bonded to a solid second phase (1) by metallic clusters (2), said second phase being permeable to electromagnetic waves; (b) irradiating the second phase (1) with electromagnetic waves; and (c) determining the change in the properties of the reflected electromagnetic waves.

32 Claims, 2 Drawing Sheets

METHOD AND DEVICE FOR IDENTIFYING A POLYMER

The invention relates to a method and a device for identifying a first polymer which is bound to a first phase which reflects electromagnetic waves.

WO 98/48275 discloses an optical sensor which can be used for detecting nucleic acids and proteins and their ligands. For the detection, the optical sensor is, for example, dipped into a nucleic acid-containing solution. After the sensor has been rinsed and dried, its optical property can then be determined. The method using the known sensor requires several steps; it is time-consuming.

WO 97/04129 discloses a method for detecting nucleic acid sequences; in this method, a first nucleic acid sequence is immobilized on a solid surface. The hybridization with a second complementary nucleic acid sequence is detected using surface-sensitive detection methods under specific conditions. WO 91/02981 describes a method for detecting an analyte using surface plasmon resonance spectroscopy. In this case too, an analyte is immobilized on a metal surface. For the detection, the analyte has in turn to be brought into contact with a solution.

In addition, U.S. Pat. No. 5,485,277 discloses a sensor for carrying out surface plasmon resonance spectroscopy. The sensor possesses a planar wave conductor which possesses a large number of reflector surfaces.

The object of the invention is to eliminate the disadvantages of the prior art. The intention is, in particular, to specify a method and a device which can be used to rapidly and readily detect polymers, in particular biochemical molecules, which are bound to a solid phase.

This object is achieved by means of the features in claims 1 and 15. Expedient refinements of the invention ensue from the features in claims 2 to 14 and 16 to 28.

In accordance with the invention, a method is provided for identifying a first polymer which is bound to a first phase which reflects electromagnetic waves, which method has the following steps:
a) bringing the first polymer into contact with a second polymer which has affinity for the first polymer and which is bound, by way of metallic clusters, to a solid second phase which is pervious to electromagnetic waves,
b) irradiating the second phase with electromagnetic waves, and
c) detecting the change in the properties of the reflected electromagnetic waves.

According to the method according to the invention, the polymer to be detected, for example a biochemical molecule, does not necessarily have to be present in solution. It can, for example, also be bound, for labeling purposes, to a solid body, such as a banknote. By simply bringing into contact the second electromagnetic wave-pervious phase and measuring the optical properties of the reflected light, it is possible to determine immediately whether the polymer which is to be detected is bound to the first solid phase. The method can be carried out rapidly and simply.

Advantageously, the electromagnetic waves employed consist of light, preferably LASER light. The properties of reflected light can be determined in a particularly simple manner.

The property change which is measured can be the absorption in a predetermined spectrum before and/or after the first and second polymers have been brought into contact. Furthermore, when monochromatic light is used, the property change which is measured can be the spectral shift. Furthermore, the property change which is measured can be the chronological change in the absorption and/or reflection when the first and second polymers are brought into contact and/or separated. The property change can be measured under several angles of incidence which differ from each other. It is also possible to conceive of measuring other changes in the properties of the reflected light. The choice of which change is detected depends on the given circumstances.

The metallic clusters can either be evaporation-coated directly onto the second phase or else be bound to the second phase by way of a layer which is formed from the second polymer. A layer which is formed from the second polymer can be applied to the surface of the second phase. The second polymer can, for example, be poly(D-glucosamine). At least one layer which is formed from the first polymer can be intercalated between the layer which is applied to the surface and the layer which is bonded to the metallic clusters. A layer sequence which is formed from the first and the second polymers can also be intercalated. The provision of such a layer sequence contributes to the formation of signals which can be identified particularly clearly and rapidly. A layer formed from the first polymer can be applied to the surface of the first phase. The surface can be formed from an oxide layer of the metal, for example from an aluminum oxide layer. A layer sequence formed from the first and second polymers can also be provided on the surface, with it being possible for the outermost layer and the layer which is bound to the surface to be formed from the first polymer. The first polymer can, for example, be polyacrylic acid (=PAA).

A polynucleotide molecule such as DNA, RNA, ssDNA, ssRNA or synthetic analogs thereof, protein, peptide, peptide nucleic acid (PNA) or a ligand thereof, or polyacrylic acid, poly(D-glucosamine) or polyethylenimine, is expediently used as the first and/or second polymer. In principle, all biochemical molecules having recombinant properties are particularly suitable.

In the step designated with the letter a, at least one further polymer which is bound to the first phase can also be brought into contact with the second polymer. This makes it possible to carry out a plurality of identification experiments simultaneously. Thus, the polymers can be used, for example, to form a barcode or a similar pattern on the surface of, for example, the first phase.

According to the invention, it is provided, in a device for identifying a first polymer which is bound to a first phase which reflects electromagnetic waves, that a second polymer, which has affinity for the first polymer, is bound, by way of metallic clusters, to the surface of a second phase which is pervious for electromagnetic waves.

The device according to the invention enables a first polymer to be identified rapidly and simply. There is no need to rinse and dry the device in order to measure the optical properties of the electromagnetic waves employed. Affinity is understood as meaning that the polymers can, by means of interactions, assume a bound or associated state. Such bonds can, for example, be hydrogen bonds, ionic bonds, hydrophobic bonds or covalent bonds. Other suitable bonds are complex bonds or bonds which are elicited by stearic effects. For example, the strains which are complementary to each other and which are present in biomolecules, such as DNA, are regarded as having affinity to each other; they are able to hybridize.

It has proved to be expedient to form the metallic clusters from silver, gold, aluminum, copper or indium. Polymers bind particularly well to these metals.

It is possible to use light, preferably LASER light, as the electromagnetic waves. Advantageously, the second phase is produced from a transparent material, such as plastic or glass. The first and/or second polymer can be DNA, RNA, protein, peptide, peptidenucleic acid or a ligand thereof, or polyacrylic acid, poly(D-glucosamine) or polyethylenimine. However, the polymer employed can also be ssDNA or ssRNA or synthetic analogs thereof.

A contrivance for determining the optical properties of the reflected light can be provided as an additional component of the device. The contrivance can be used to measure the absorption in a predetermined spectrum before and/or after the first and the second polymers have been brought into contact. In addition, the contrivance can be used to measure the spectral shift of the reflected light.

Expediently, the contrivance can be used to measure the optical property at several angles of incidence which differ from each other.

The metallic clusters can be bound to the second phase by way of a layer which is formed from the second polymer. Furthermore, a layer formed from the second polymer can be applied to the surface of the second phase. Expediently, at least one layer which is formed from the first polymer is also intercalated between the layer which is provided on the surface and the layer which is bound to the metallic clusters. A layer which is formed from the first polymer can be applied to the surface of the first phase and/or a layer which is formed from the second polymer can be applied to the layer which is provided on the surface. The layer complex which is described makes labeling possible and also makes it possible to identify the label simply and rapidly.

The invention is explained in more detail below with the aid of the exemplary embodiment which is depicted in the drawing. In the drawing.

Figure 1:
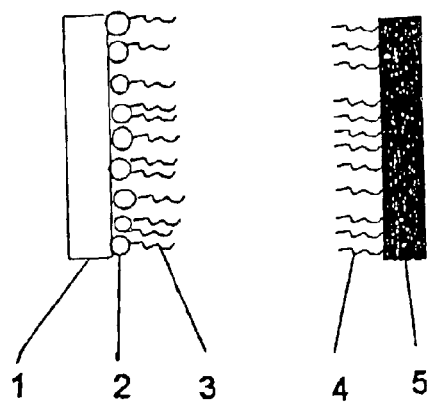
FIG. 1 shows a diagrammatic view of a device.
Figure 2:
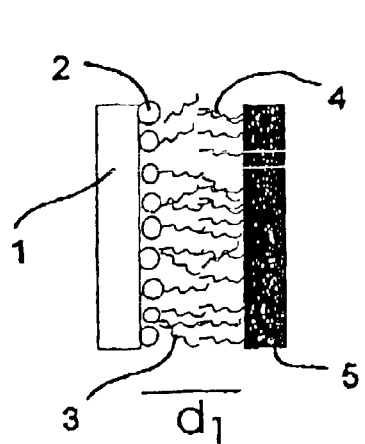
FIG. 2 shows the device according to FIG. 1 in the non-hybridized case.
Figure 3:
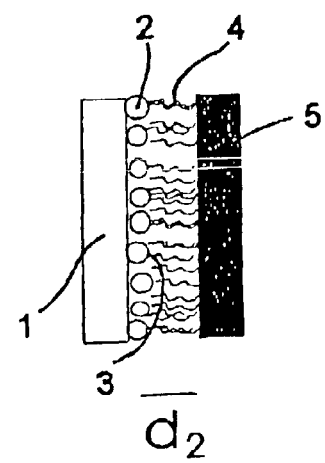
FIG. 3 shows the device according to FIG. 1 in the hybridized case.

In FIGS. 1–3, a second solid phase is produced, for example, from a glass support 1. Metallic clusters 2, for example gold clusters, are present on one surface of the glass support 1. A single-stranded DNA 3 is bound, as the second polymer, to the clusters 2. Another single-stranded DNA 4 is bound, as the first polymer, to a metal strip 5. The metal strip 5 can, in turn, be fixed, for example for labeling purposes, to banknotes (not depicted here).

Provided the DNA 3 and the other DNA 4 are brought into contact, two cases can be distinguished:

In the first case, which is shown in FIG. 2, the DNA 3 is not complementary to the other DNA 4. No hybridization takes place. A first distance $d_1$ arises between the layer formed by the clusters 2 and the metal strip 5.

In the second case, which is shown in FIG. 3, the DNA 3 is complementary to the other DNA 4. The DNA 3 and the other DNA 4 hybridize. A smaller, second distance $d_2$ arises between the layer formed by the clusters 2 and the metal strip 5.

A laser beam (not depicted here) which is incident through the glass support 1 is reflected at the [lacuna] by the metal strip 5. The properties of the reflected light depend on the distance $d_1$ or $d_2$ of the layer formed by the clusters 2 from the metal strip 5. Thus, the absorption, for example, is altered. By measuring the absorption, it is then possible to determine, in a simple manner, whether a hybridization is present or not. This makes it possible to identify the first polymer 4.

In order to produce the optical probe shown in FIGS. 1–3, a glass support 1 is sputtered with gold. For this, the glass support 1 is suspended in a vacuum chamber in which gold foil is placed at the same time. After the vacuum chamber has been pumped down to $10^{-2}$ mbar and subsequently flushed with argon gas, the pressure in the vacuum chamber is adjusted to about $10^{-1}$ mbar. After that, a plasma is ignited, resulting in gold atoms being sputtered out of the foil. The gold atoms become deposited on the surface of the glass support 1. At a sputter current of 40 mA, a gold film having a mass thickness of 5 nm is formed after about 10 seconds. After that, the gold film is healed at about 200° C. Round gold clusters 2, which are suitable for the desired color intensification effect, are formed. Subsequently, the glass support 1, which is coated with gold clusters 2, is dipped into a solution which contains oligonucleotides 3 which are provided with a thiol group at their 5' ends. The oligonucleotides 3 settle on the gold clusters with the formation of a thiol bond.

An aluminum substrate 5 is, for example, used for producing the sample designated by the reference numbers 4 and 5. Using a defined electrochemical oxidation of the aluminum substrate 5, for example in 5% oxalic acid at 300 mA and about 50 V, oxide layers of different thicknesses are generated by immersing the aluminum substrate 5 more deeply, in a stepwise manner, into the solution. As a consequence of interference effects, these oxide layers have different colors.

In order to covalently couple other oligonucleotides 4, which are provided with amino groups at their 5' ends, the oxide layers are coated with a layer which carries a free amino group. For this, the aluminum substrate 5 is immersed, for about 30 minutes, in an approximately 10% aqueous solution of aminopropyl triethoxysilane at a pH of about 9. The aluminum substrate is subsequently washed with water and dried for one hour in a drying oven at about 80° C.

The silanized aluminum substrates 5 which are produced in this way are then incubated for 12 hours in a 2.5% solution of glutardialdehyde which contains 50 mmol of $NaCNBH_3/l$. After that, they are washed thoroughly with water.

In order to bind on the other oligonucleotide 4, the aluminum substrates 5 are incubated overnight, at 4° C., in an aqueous buffer solution which contains other oligonucleotides 4 at a concentration of 1 µmol/l, 0.1×PBS buffer and 50 mmol of $NaCNB_3/l$. After that, the aluminum substrates 5 are thoroughly rinsed once again with water. They then possess covalently bonded other oligonucleotides 4 on their surface.

With regard to other details, in particular the size of the cluster 2 and the distance parameters, the reader is referred to WO 98/48275, the disclosure content of which is hereby incorporated by reference.

In order to detect a hybridization between the DNA 3, or the detector oligonucleotide, and the other DNA 4, or the labeling oligonucleotide, the glass support 1 and the metal strip 5, e.g. the aluminum substrate which has been prepared by the above-described method, are pressed onto each other. As a consequence of different distances between the reflecting aluminum surface and the gold clusters 2, it is possible to recognize characteristic color patterns. These make it possible to conclude whether there is or is not hybridization between the labeling oligonucleotide and the detector oligonucleotide.

Figure 4:
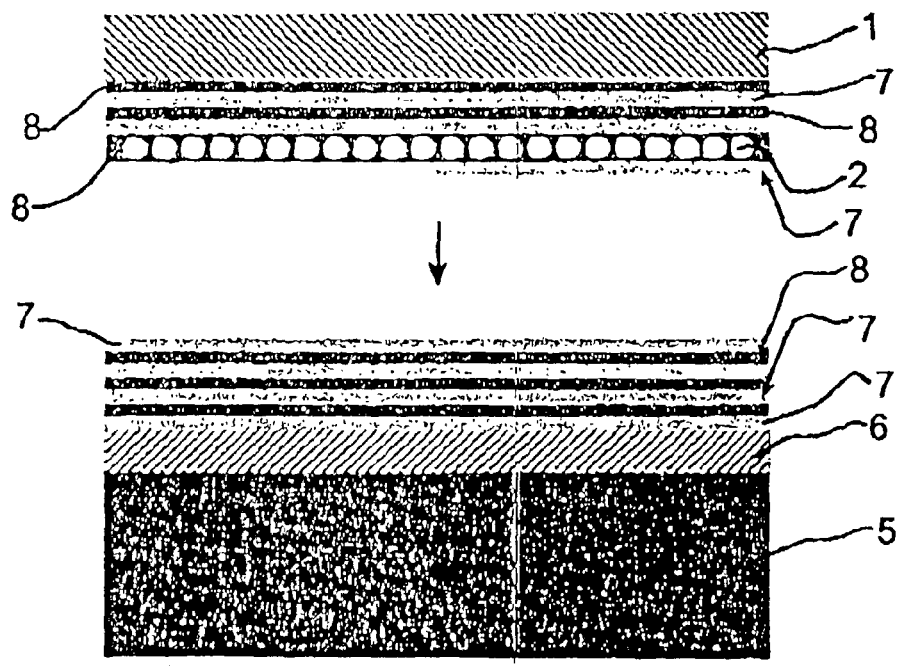
FIG. 4 shows a diagrammatic view of another device.

FIG. 4 shows another exemplary embodiment of the invention. An aluminum oxide layer 6 is located on a metal strip 5 prepared from aluminum. The aluminum oxide layer 6 is covered by a PAA layer 7. On top of this there then comes a poly(D-glucosamine) layer 8. Several such layer sequences consisting of PAA and poly(D-glucosamine) are provided. The uppermost layer is formed by a PAA layer 7.

The probe consists of a glass support 1 which forms the substrate. A poly(D-glucosamine) layer 8 is provided on its surface. On top of that lies a PAA layer 7. Several layer sequences consisting of poly(D-glucosamine) 8 and PAA 7 are provided. Gold clusters 2 are bonded on a poly(D-glucosamine) layer 8 in the vicinity of the surface. On top of this there lies a further poly(D-glucosamine) layer 8. For test purposes, a section of this layer is overlaid with a PAA layer 7.

In order to produce the coated aluminum strip 5, the latter is coated by immersing it alternately in a polyacrylic acid-containing solution and in a poly(D-glucosamine) solution. In each case, the coating time was 15 minutes and the concentration of the solutions was 0.5 g/l. For coating with the gold clusters 2, the probe is immersed in a solution which contains approximately 0.4% gold clusters having a diameter of 25 nm. The gold clusters 2 bind by means of adsorptive forces. The probe is subsequently immersed once again in a poly(D-glucosamine) solution such that the gold clusters are packed into the layer sequence. For the purpose of detecting that the method is working, the probe is dipped to half its extent into PAA. In this way, a section of the probe is coated with a PAA layer 7.

In the above-described arrangement, the label is applied to the probe for the sake of clarity. In practice, the label will be provided in an analogous manner on the sample.

Figure 5:
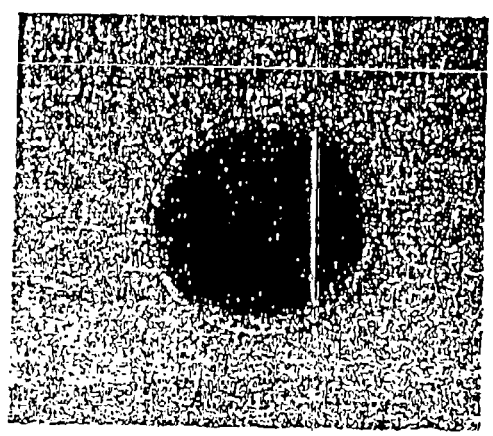
FIG. 5 shows the detection of a label.

FIG. 5 shows the contact of the circular probe with the coated aluminum oxide substrate 5. In the figure, it is possible to discern a boundary line running from the top left to the bottom right. The light region corresponds to the region of the probe which is coated with a poly(D-glucosamine) layer 8. The dark region corresponds to the section of the probe which carries the PAA layer 7 on its surface. The repulsive interaction between the superficial PAA layer 7 on the probe and the PAA layer 7 on the substrate results in a light reflection which is different from that in the contact region of the poly(D-glucosamine) layer 8 on the probe, which layer interacts attractively with the PAA layer 7 on the aluminum substrate 5. It is consequently possible to distinguish clearly whether a label which is formed, for example, from PAA or another polymer, in particular a biopolymer, and which is applied to the aluminum substrate 5 has affinity to the probe.

The invention claimed is:

1. A method for identifying a first polymer which is bound to a first phase which reflects electromagnetic waves, which method has the following steps:
    a) bringing the first polymer into contact with a second polymer which has affinity to the first polymer and which is bound, by way of metallic clusters, to a solid second phase which is pervious to electromagnetic waves,
    b) irradiating the second phase with electromagnetic waves, and
    c) detecting a change in the properties of the reflected electromagnetic waves, wherein the change in the properties of the reflected electromagnetic waves identifies the first polymer.

2. The method as claimed in claim 1, characterized in that light is used as the electromagnetic waves.

3. The method as claimed in claim 1, characterized in that the property change which is measured is the absorption in a predetermined spectrum before and/or after the first polymer has been brought into contact with the second polymer.

4. The method as claimed in claim 1, characterized in that the property change which is measured is the chronological change in the absorption and/or reflection when the first polymer and the second polymer are brought into contact and/or separated.

5. The method as claimed in claim 1, characterized in that the property change is measured at several angles of incidence which differ from each other.

6. The method as claimed in claim 1, characterized in that the metallic clusters are evaporation-coated directly onto the second phase or are bound to the second phase by way of a layer which is formed from the second polymer.

7. The method as claimed in claim 6, characterized in that a layer formed from the second polymer is applied to the surface of the second phase.

8. The method as claimed in claim 7, characterized in that at least one layer formed from the first polymer is intercalated between the layer which is applied to the surface and the layer which is bonded to the metallic clusters.

9. The method as claimed in claim 1, characterized in that a layer formed from the first polymer is applied to the surface of the first phase.

10. The method as claimed in claim 9, characterized in that a layer sequence formed from the first polymer and the second polymer is applied to the surface.

11. The method as claimed in claim 1, characterized in that the first polymer and/or second polymer employ and/or employs DNA, RNA, ssDNA or ssRNA or synthetic analogs thereof, protein, peptide, peptide nucleic acid (PNA) or a ligand thereof, or polyacrylic acid, polyethylenimine or poly(D-glucosamine).

12. The method as claimed in claim 1, characterized in that, in the step denoted with the letter a, at least one other polymer, which is bound to the first phase, is brought into contact with the second polymer.

13. The method as claimed in claim 12, characterized in that the polymers are applied to the first phase in the form of a barcode.

14. A device for identifying a first polymer which is bound to a first phase which reflects electromagnetic waves, characterized in that a second polymer, which has affinity to the first polymer, is bound, by way of metallic clusters, to the surface of a second phase which is pervious to electromagnetic waves.

15. The device as claimed in claim 14, characterized in that the metallic clusters are formed from silver, gold, aluminum, copper or indium.

16. The device as claimed in claim 14, characterized in that the electromagnetic waves are light.

17. The device as claimed in claim 14, characterized in that the second phase is produced from a transparent material.

18. The device as claimed in claim 14, characterized in that the first polymer and/or the second polymer is/are DNA, RNA, ssDNA or ssRNA or synthetic analogs thereof, protein, peptide, peptidenucleic acid (PNA) or a ligand thereof, or polyacrylic acid, poly(D-glucosamine) or polyethylenimine.

19. The device as claimed in claim 14, characterized in that a contrivance for determining the optical property of the reflected light is provided.

20. The device as claimed in claim 19, characterized in that the contrivance can be used to measure the absorption in a predetermined spectrum before and/or after the first polymer and the second polymer are brought into contact.

21. The device as claimed in claim 19, characterized in that the contrivance can be used to measure the spectral shift of the reflective light.

22. The device as claimed in claim 19, characterized in that the contrivance can be used to measure the optical property at several angles of incidence which differ from each other.

23. The device as claimed in claim 14, characterized in that the metallic clusters are bound to the second phase by way of a layer which is formed from the second polymer.

24. The device as claimed in claim 23, characterized in that a layer which is formed from the second polymer is applied to the surface on the second phase.

25. The device as claimed in claim 24, characterized in that at least one layer which is formed from the first polymer is intercalated between the layer provided on the surface and the layer which is bonded to the metallic clusters.

26. The device as claimed in claim 14, characterized in that a layer which is formed from the first polymer is applied to the surface of the first phase.

27. The device as claimed in claim 26, characterized in that a layer which is formed for the second polymer is applied to the layer which is provided on the surface.

28. The method as claimed in claim 2, wherein said light is LASER light.

29. The method as claimed in claim 2, wherein said light is monochromatic light.

30. The method as claimed in claim 29, wherein said property change which is measured is the spectral shift of said monochromatic light.

31. The device as claimed in claim 16, wherein said light is LASER light.

32. The device as claimed in claim 17, wherein said transparent material is plastic or glass.

* * * * *